(12) United States Patent
Dalmases Barjoan et al.

(10) Patent No.: US 8,653,280 B2
(45) Date of Patent: Feb. 18, 2014

(54) PROCESS FOR THE PREPARATION OF ASENAPINE

(75) Inventors: Pere Dalmases Barjoan, Sant Feliu de Llobregat (ES); Juan Huguet Clotet, Sant Joan Despi (ES); Jordi Peirats Masia, Barcelona (ES)

(73) Assignee: Laboratories Lesvi, S.L., Sant Joan Despi (ES)

( * ) Notice: Subject to any disclaimer, the term of this patent is extended or adjusted under 35 U.S.C. 154(b) by 0 days.

(21) Appl. No.: 13/812,212

(22) PCT Filed: Jul. 29, 2011

(86) PCT No.: PCT/EP2011/063071
§ 371 (c)(1),
(2), (4) Date: Mar. 28, 2013

(87) PCT Pub. No.: WO2012/013766
PCT Pub. Date: Feb. 2, 2012

(65) Prior Publication Data
US 2013/0225835 A1 Aug. 29, 2013

Related U.S. Application Data

(60) Provisional application No. 61/370,506, filed on Aug. 4, 2010.

(30) Foreign Application Priority Data

Jul. 29, 2010 (EP) .................... 10171222

(51) Int. Cl.
C07D 491/044 (2006.01)
C07D 313/14 (2006.01)

(52) U.S. Cl.
USPC .......................... 548/453; 549/354

(58) Field of Classification Search
None
See application file for complete search history.

(56) References Cited

U.S. PATENT DOCUMENTS

| 4,145,434 A | 3/1979 | Van Der Burg |
| 2006/0229352 A1 | 10/2006 | Kemperman et al. |
| 2011/0046393 A1 | 2/2011 | Wang et al. |

FOREIGN PATENT DOCUMENTS

| EP | 1710241 | 10/2006 |
| WO | WO95/23600 | 9/1995 |
| WO | WO99/32108 | 7/1999 |
| WO | WO 2006106136 A1 * | 10/2006 |
| WO | WO2009/008405 | 1/2009 |

OTHER PUBLICATIONS

Funke, et al., "Physico-Chemical Properties and Stability of Trans-5-Chloro-2-Methyl-2,3,3a,12b-Tetrahydro-1H-Dibenz[2,3 : 6,7]Oxepino[4,5-c]Pyrrolidine Maleate", 1999, Arzneim.-Forsch./Drug Res., No. 40, pp. 536-539.
PCT Search Report and Written Opinion for PCT/EP2011/063071, completed Aug. 19, 2011.
Van Der Linden, Marco, et al., "Debottlenecking the Synthesis Route of Asenapine", 2008, Organic Process Research and Development, No. 12, pp. 196-201.

* cited by examiner

Primary Examiner — Michael Barker
(74) Attorney, Agent, or Firm — Barnes & Thornburg LLP

(57) ABSTRACT

The present invention is directed to novel compounds of formula (I) as well as to the process for their preparation. Novel compounds of formula (I) can be converted into asenapine through an efficient process. The invention also relates to novel intermediates used in this process and their use in the preparation of compounds of formula (I).

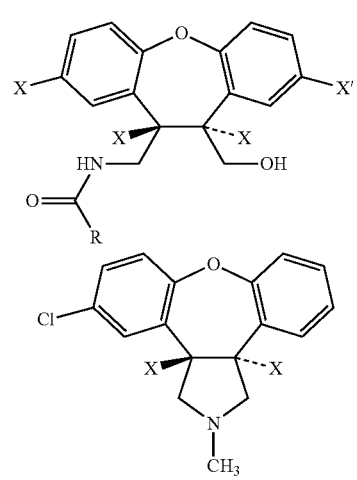

Asenapine

14 Claims, No Drawings

PROCESS FOR THE PREPARATION OF ASENAPINE

CROSS-REFERENCE TO RELATED APPLICATIONS

This application is a national stage entry under 35 U.S.C. §371(b) of International Application No. PCT/EP2011/063071, filed Jul. 29, 2011, which claims the benefit of European Patent Application Serial No. 10171222.2, filed Jul. 29, 2010 and U.S. Provisional Application Ser. No. 61/370,506, filed Aug. 4, 2010, the disclosures of all of which are hereby incorporated herein by reference.

FIELD OF THE INVENTION

The present invention is directed to novel compounds of formula I and their use as intermediates in the synthesis of asenapine. The invention provides a process for the preparation of these novel compounds of formula I and their conversion to asenapine.

BACKGROUND OF THE INVENTION

Asenapine or trans-5-chloro-2-methyl-2,3,3a,12b-tetrahydro-1H-dibenz[2,3:6,7]oxepino[4,5-c]pyrrole is described in U.S. Pat. No. 4,145,434 to van der Burg and it is represented by the following chemical structure:

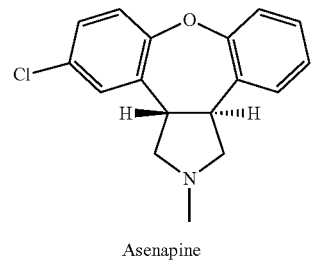 [SMILES: CN1C[C@@H]2c3ccccc3Oc3ccc(Cl)cc3[C@H]2C1]

Asenapine

Asenapine has CNS-depressant activity and it has antiserotonin activity. Asenapine exhibits potential antipsychotic activity and may be useful in the treatment of depression (see international patent application WO 99/32108). It has been established that the maleate salt of asenapine is a broad spectrum, high potency serotonin, noradrenaline and dopamine antagonist. A pharmaceutical preparation suitable for sublingual or buccal administration of asenapine maleate has been described in the international patent application WO 95/23600. Asenapine maleate is launched in the USA for two related indications. It is indicated for the acute treatment of schizophrenia in adults as well as for the treatment of manic or mixed episodes associated with bipolar I disorder, with or without psychotic features also in adults.

The synthetic approach for the preparation of asenapine is derivable from the teaching of U.S. Pat. No. 4,145,434 and disclosed in full Example 9 of EP 1 710 241. The last steps of this methodology are shown in the following scheme.

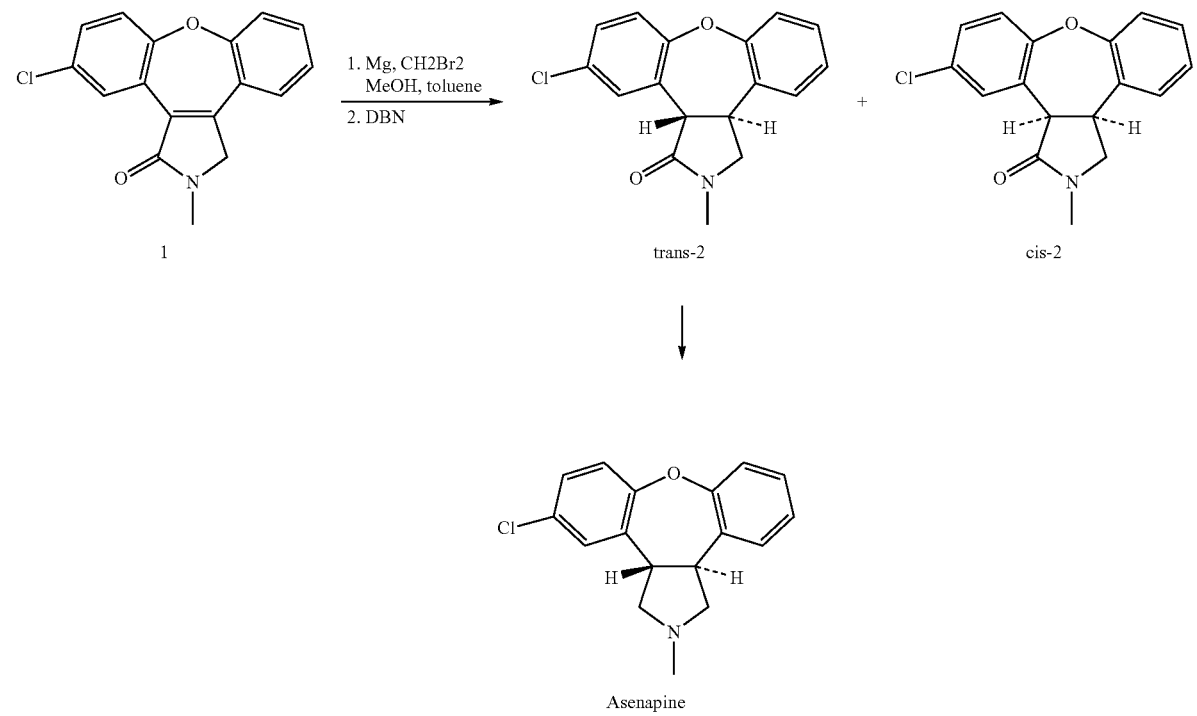

Scheme 1

In Scheme 1, the double bond in the enamide, 11-chloro-2,3-dihdyro-2-methyl-1H-dibenzo[2,3;6,7]oxepino[4,5-c]pyrrol-1-one (1), is reduced to produce a mixture of a desired trans-2-isomer and an unwanted cis-2-isomer, in a 1:4 ratio. The unfavourable product ratio can be improved by subsequent partial isomerisation of the unwanted cis-2-isomer into the trans-2-isomer using DBN, leading to a thermodynamic equilibrium ratio of trans to cis of 1:2. Separation of the trans-isomer and the cis-isomer is done by chromatography over silica gel. The cis-isomer can be isomerized again using DBN and the resulting trans-isomer is again separated by chromatography. The drawback of this process is that it is extremely elaborate and time-consuming, while the final yield of the trans-isomer is only moderate.

European patent EP 1 710 241 discloses preparation of asenapine which avoids the separation of the cis-trans isomers through chromatography over silica gel. In Scheme 2, the cis-trans mixture of the compound 2 and/or its regio-isomer, 2a, preferably without separating the enantiomers, undergoes the ring-opening reaction by an excess of strong base in an alcoholic medium, yielding, predominantly, a trans-isomer of the amino-acid of the formula 3 or 3a in an approx. ratio 10:1 (trans:cis), respectively.

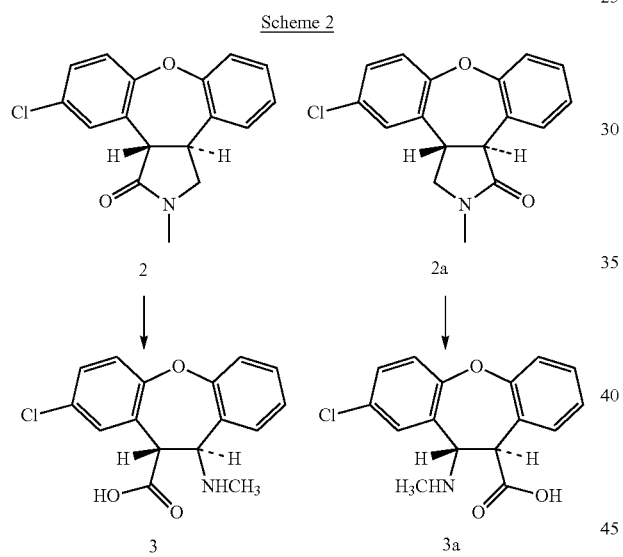

Scheme 2

The trans-3 or the trans-3a may be isolated and subjected to re-cyclisation yielding the desired trans-2 or trans-2a with the overall yield of about 60% in respect of compound 1. Alternatively, compounds trans-3 or trans-3a may be converted to asenapine directly, by cyclisation with a reducing agent, optionally with a combination with a Lewis acid. In conclusion, in order to obtain the desired trans-isomer it is necessary to carry out a complex procedure involving first ring-opening to the transform and then re-cyclisation.

International patent application WO 2009/008405 provides a process for the production of asenapine in which reduction, leaving group conversion, hydrogenation and methylation are carried out in that order (see Scheme 3; $X^1$ and $X^2$ are the same or different and each independently represents hydrogen or halogen atom; R represents an alkyl group optionally substituted; Y represents a leaving group).

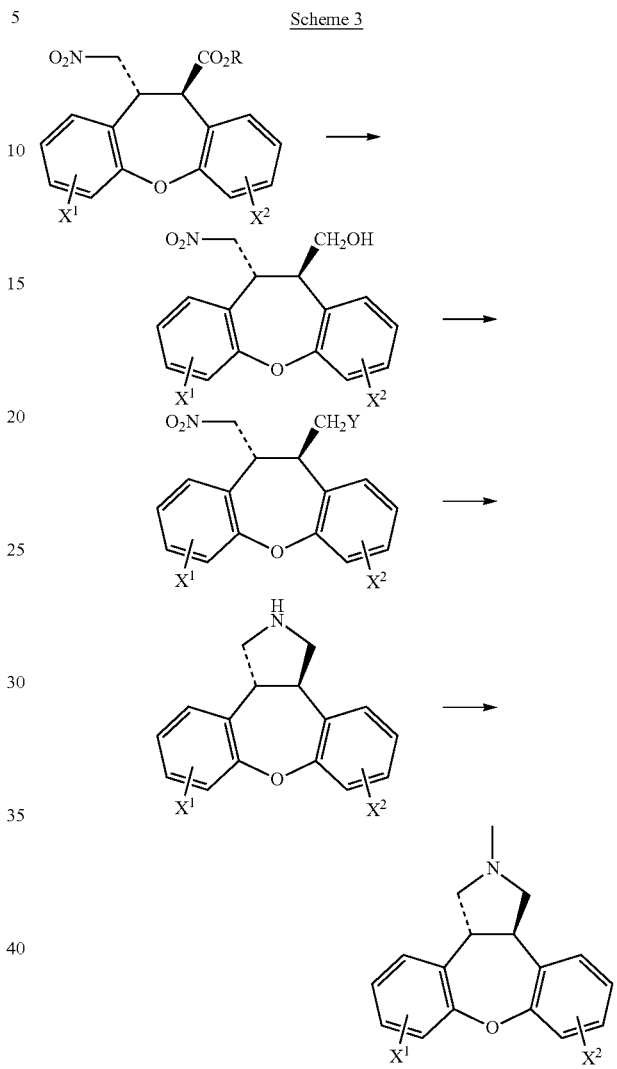

Scheme 3

There is a need for an industrially efficient process for the preparation of asenapine with good esteroselectivity and yields.

BRIEF DESCRIPTION OF THE INVENTION

The present inventors have surprisingly found that the process of the invention provides asenapine with a good yield which makes it appropriate for the preparation of asenapine or salts thereof in an industrial scale.

Thus, a first aspect of the present invention relies on a compound of formula I

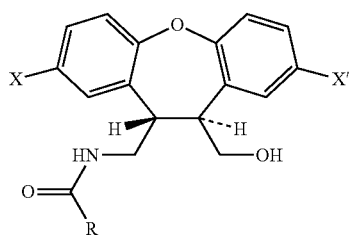

I wherein X and X' are different and each independently represents hydrogen or chlorine atom and R is selected from hydrogen or a substituted or unsubstituted $C_1$-$C_6$ alkyloxy group.

A second aspect of the invention relates to process for preparing compound of formula I comprising reacting an amino alcohol compound of formula II

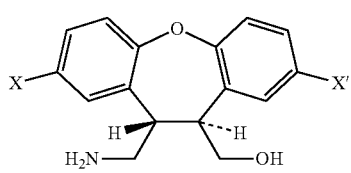

II wherein X and X' have the same definitions as above with a formic acid anhydride of formula III or a chloroformate of formula IV

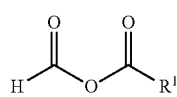

III

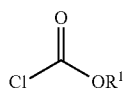

IV wherein $R^1$ is a substituted or unsubstituted $C_1$-$C_6$ alkyl.

Another aspect of the invention is a process for preparing asenapine or its salts

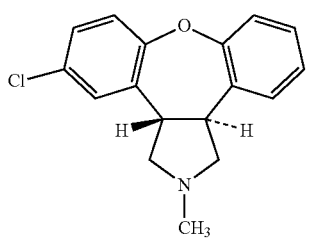

Asenapine comprising:
(a) reducing the carbonyl moiety of a compound of formula I

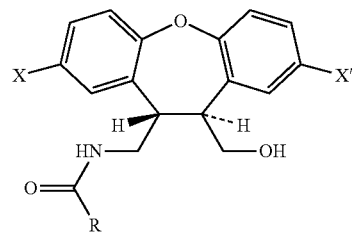

I wherein X, X' and R have the same definitions as above to give a methylamino compound of formula V

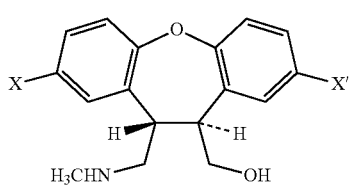

V wherein X and X' have the same definitions as above
(b) optionally, converting the hydroxyl moiety of compound V into a leaving group to give a compound of formula VI

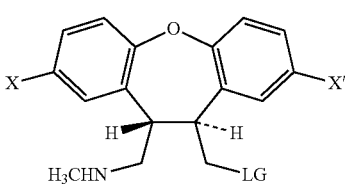

VI wherein X and X' have the same definitions as above and LG is a leaving group
(c) cyclising the compound of formula V or VI to give asenapine; and
(d) optionally, converting the asenapine to a salt thereof, or
(a-i) converting the hydroxyl moiety of compound of formula I into a leaving group to give a compound of formula VIII

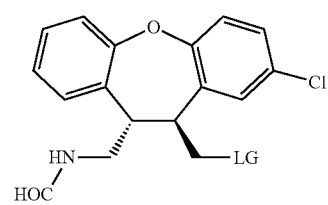

VIII wherein LG is a leaving group
(b-i) reducing and cyclising the compound of formula VIII to give asenapine; and
(c-i) optionally, converting the asenapine to a salt thereof.

Another aspect of the invention relies on a process for preparing asenapine or its salts comprising treating compound of formula I with a reducing agent.

An aspect of the invention relates to amino alcohol compound of formula II:

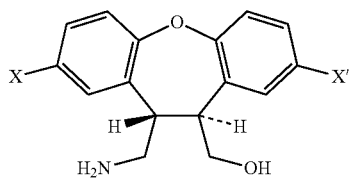

wherein X and X' have the same definitions as above.

Another aspect of the invention is directed to a compound of formula V:

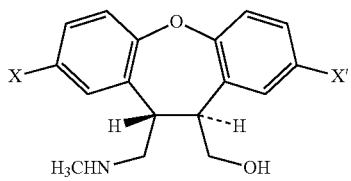

wherein X and X' have the same definitions as above.

Another aspect is a compound of formula VI:

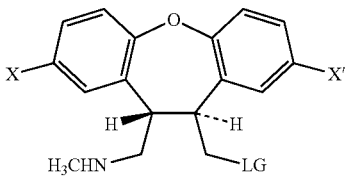

wherein X, X' and LG have the same definitions as above.

Another aspect of the invention is directed to compound of formula VIII

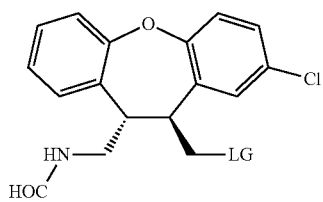

wherein LG is a leaving group.

Another aspect of the invention is a process for the preparation of compound I wherein amino alcohol compound of formula II, is prepared by reduction of both the nitro and ester functions of a compound of formula VII

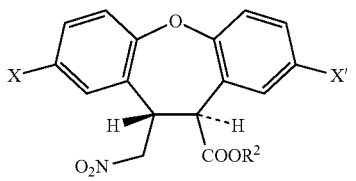

wherein X and X' have the same definitions as above and $R^2$ represents a substituted or unsubstituted $C_1$-$C_6$ alkyl.

The invention also relies on the use of novel intermediates I, V, VI and VIII in the preparation of asenapine or salts thereof.

The invention also relies on the use of compound II in the preparation of compound of formula I.

DESCRIPTION OF THE INVENTION

Definitions

In the context of the present invention, the following terms have the meaning detailed below:

The term "leaving group" refers to a group that can easily be replaced by another group. In J. March Advanced Organic Chemistry, 4th edition, 1992, are listed some typical leaving groups. In the context of the present invention, the leaving groups are preferably selected from halogens and activated alcohols, such as sulfonyloxy groups. The halogens include fluorine, chlorine, bromine and iodine. The sulfonyloxy group is represented by —$OSO_2R'$, wherein R' is a substituted or unsubstituted alkyl, a substituted or unsubstituted aryl, a fluorinated hydrocarbon or a halogen. By the term "substituted or unsubstituted alkyl" it is understood a linear hydrocarbon radical consisting of carbon and hydrogen atoms, which does not contain unsaturation, having one to twelve carbon atoms and which is joint to the rest of the molecule by a single bond. Alkyl radicals may be optionally substituted by one or more substituents such as an aryl, halo, hydroxy, alkoxy, carboxy, cyano, carbonyl, acyl, alkoxycarbonyl, amino, nitro, mercapto, alkylthio, etc. The term "substituted or unsubstituted aryl" relates to an aromatic hydrocarbon radical containing from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

The term substituted or unsubstituted alkyl- or aryl-sulfonyl halide is understood as containing a sulfonyloxy group, represented by —$OSO_2R'$, as defined above, and a halide ion selected from fluoride, chloride, bromide and iodide.

By the term "$C_1$-$C_6$ substituted or unsubstituted alkyloxy" it is understood a linear hydrocarbon radical consisting of carbon and hydrogen atoms, which does not contain unsaturation, having one to six carbon atoms and which is joint to the rest of the molecule by an oxygen atom. Alkyloxy radicals may be optionally substituted by one or more substituents such as an aryl, halo, hydroxy, alkoxy, carboxy, cyano, carbonyl, acyl, alkoxycarbonyl, amino, nitro, mercapto, alkylthio, etc. Examples of "$C_1$-$C_6$ substituted or unsubstituted alkyloxy" are methoxy, ethoxy, propoxy, butoxy, sec.-butoxy, tert.-butoxy, trichloromethoxy, 1-phenylpropoxy, 2-phenylethoxy and phenylmethoxy.

By the term "$C_1$-$C_6$ substituted or unsubstituted alkyl" it is understood a linear hydrocarbon radical consisting of carbon and hydrogen atoms, which does not contain unsaturation, having one to six carbon atoms and which is joint to the rest of the molecule by a single bond. Alkyl radicals may be optionally substituted by one or more substituents such as an aryl, halo, hydroxy, alkoxy, carboxy, cyano, carbonyl, acyl, alkoxycarbonyl, amino, nitro, mercapto, alkylthio, etc.

The term "one-pot process" means two or more reactions that take place without isolating intermediate compounds, wherein all the reactants are added at the beginning of the first reaction or adding all reactants sequentially during the course of the reaction.

Ether solvents include diethyl ether, tert-butyl methyl ether, 1,2-dimethoxyethane, cyclopentyl methyl ether, diglyme and tetrahydrofuran. Amide solvents are selected from N,N-dimethylformamide, N,N-dimethylacetamide, N-methylpyrrolidone and 1,3-dimethyl-2-imidazolidinone. Ketone solvents are selected from methyl isobutyl ketone, methyl ethyl ketone, 2-propanone, cyclohexanone, and cyclopentanone. Ester solvents are selected from ethyl acetate and butyl acetate. Alcohol solvents are selected from methanol, ethanol, 1-propanol, 2-propanol, 1-butanol and 2-butanol. Halogenated solvents are selected from dichloromethane, 1,2-dichloroethane, and chloroform. Aromatic hydrocarbon solvents are selected from toluene, xylene, chlorobenzene and nitrobenzene.

As organic bases there may be mentioned tertiary amines (trimethylamine, triethylamine, diisopropylethylamine, tributylamine, N-methylmorpholine and 1,4-diazabicyclo[2.2.2]octane), aromatic amines (pyridine, 2-methyl-5-ethylpyridine, 2,6-di-tert-butylpyridine, 4-dimethyl aminopyridine, imidazole and 1-methylimidazole), cyclic amidines (1,8-diazabicyclo[5.4.0]-7-undecene, 1,5-diazabicyclo[4.3.0]-5-nonene), alkali metal alkoxides (lithium methoxide, sodium methoxide, potassium methoxide, lithium ethoxide, sodium ethoxide, potassium ethoxide and lithium tert-butoxide) and alkali metal amides (lithium diisopropylamide, lithium hexamethyldisilazide, potassium hexamethyldisilazide).

As examples of inorganic bases there may be mentioned alkali metal hydroxides (lithium hydroxide, sodium hydroxide, potassium hydroxide and cesium hydroxide), alkali metal carbonates (lithium carbonate, sodium carbonate, potassium carbonate and cesium carbonate), alkali metal hydrogenocarbonates (sodium hydrogenocarbonate, potassium hydrogenocarbonate), ammonia, ammonium carbonate and the like.

The term "purification" refers to the process wherein a purified drug substance can be obtained. Therefore, term "purification" comprises solvent extraction, filtration, slurring, washing, phase separation, evaporation, centrifugation, column chromatography or crystallisation.

DESCRIPTION

According to a first aspect, the present invention is directed to novel compounds of formula I

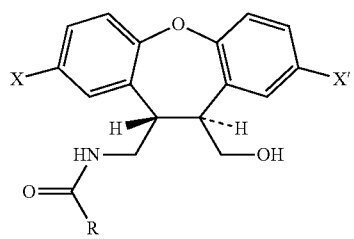

wherein X and X' are different and each independently represents hydrogen or chlorine atom and R is selected from hydrogen or a substituted or unsubstituted $C_1$-$C_6$ alkyloxy group.

Examples of compounds of formula I are trans-N-(8-Chloro-11-hydroxymethyl-10,11-dihydro-dibenzo[b,f]oxepin-10-ylmethyl)-formamide, trans-(8-Chloro-11-hydroxymethyl-10,11-dihydro-dibenzo[b,f]oxepin-10-ylmethyl)-carbamic acid benzyl ester, trans-(2-Chloro-11-hydroxymethyl 10,11-dihydro-dibenzo[b,f]oxepin-10-ylmethyl)-carbamic acid benzyl ester, trans-(8-Chloro-11-hydroxymethyl-10,11-dihydro-dibenzo[b,f]oxepin-10-ylmethyl)-carbamic acid ethyl ester or trans-(2-Chloro-11-hydroxymethyl-10,11-dihydro-dibenzo[b,f]oxepin-10-ylmethyl)-carbamic acid ethyl ester.

The second aspect of the invention is directed to a process for the preparation of compounds of formula I comprising reacting an amino alcohol compound of formula II

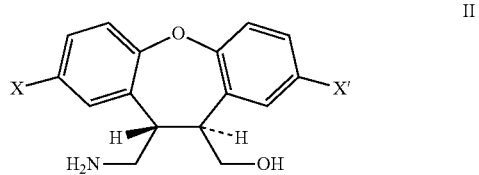

wherein X and X' have the same definitions as above with a formic acid anhydride of formula III or a chloroformate of formula IV

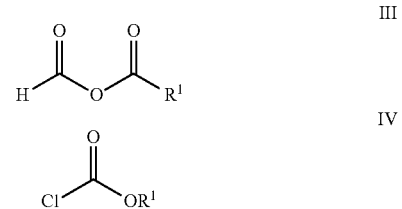

wherein $R^1$ is a substituted or unsubstituted $C_1$-$C_6$ alkyl.

Formic acid anhydrides of formula III are selected from formic acetic anhydride, formic propionic anhydride or formic isobutyric anhydride.

The reaction may be performed by the addition of a solution of compound II in an organic solvent to a solution of the formic acid anhydride of formula III in an organic solvent, with no particular restriction on the order of addition and mixing. As examples of organic solvents, there may be mentioned ether solvents, acetonitrile, ester solvents, halogenated solvents, aromatic hydrocarbon solvents, ketones and formic acid. These solvents may be used alone or two or more may be used simultaneously. The reaction temperature for the reaction is 0-150° C. and preferably 0-100° C.

As examples of chloroformates of formula IV they may be mentioned methyl chloroformate, ethylchloroformate or benzylchloroformate.

The reaction is carried out by conventional methodologies. The resulting compound of formula I may be prepared by reaction of amine compound II with a chloroformate of formula IV. The reaction may be carried out in a mixture of water and organic solvents. Suitable organic solvents include ether solvents, amide solvents, ketone solvents, ester solvents, halogenated solvents and/or aromatic hydrocarbon solvents. The reaction also requires the addition of an inorganic base. Alternatively, the reaction may be carried out in a non-protic organic solvent. Examples of non-protic organic solvents are ethyl acetate, acetonitrile, acetone, methyl ethyl ketone, tetrahydrofuran, dioxane, toluene, xylene, etc. These solvents may be used alone or two or more may be used simultaneously. The reaction also requires the presence of an organic base.

Another aspect of the invention is a process for preparing asenapine or its salts

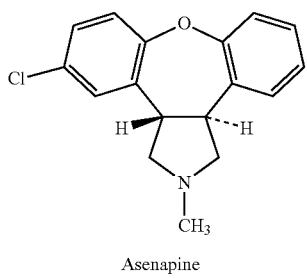 [SMILES: CN1C[C@@H]2c3ccccc3Oc3ccc(Cl)cc3[C@H]2C1]

Asenapine comprising:

(a) reducing the carbonyl moiety of compound of formula I

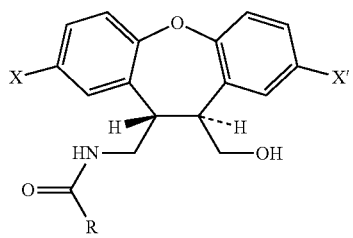

wherein X, X' and R have the same definitions as above to give a methylamino compound of formula V

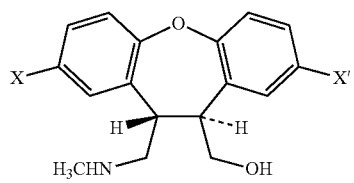

wherein X and X' have the same definitions as above (b) optionally, converting the hydroxyl moiety of compound V into a leaving group to give a compound of formula VI

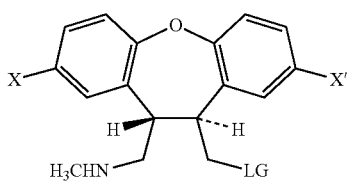

wherein X and X' have the same definitions as above and LG is a leaving group (c) cyclising the compound of formula V or VI to give asenapine; and (d) optionally, converting the asenapine to a salt thereof, or (a-i) converting the hydroxyl moiety of compound of formula I into a leaving group to give a compound of formula VIII

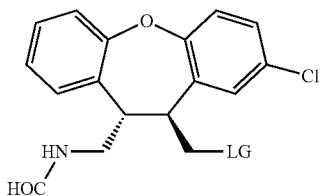

wherein LG is a leaving group (b-i) reducing and cyclising the compound of formula VIII to give asenapine; and (c-i) optionally, converting the asenapine to a salt thereof.

The reducing agent used for reducing the carbonyl moiety of compound I may be boron hydrides or aluminum hydrides. As examples of boron hydride compounds there may be mentioned alkali metal borohydrides such as lithium borohydride, sodium borohydride and potassium borohydride; and borane compounds such as diborane and borane. In most cases, the reducing agent is sodium borohydride. Examples of aluminum hydrides are lithium aluminum hydride, sodium bis-(2-methoxyethoxy)aluminum hydride, lithium tri-tert-butoxy-aluminum hydride and aluminum hydride. The amount of reducing agent used is 1-10 mol with respect to 1 mol of compound I.

Aluminum hydride, also referred to as "alane", is usually prepared as an alane•etherate complex by the reaction of lithium aluminum hydride with a Lewis acid such as aluminum trichloride, zinc chloride or with beryllium chloride. In an alternative synthesis, lithium aluminum hydride is reacted with sulphuric acid to give the alane•eherate complex.

When an alkali metal borohydride is used as the reducing agent, a Lewis acid such as boron trifluoride, a Bronsted acid such as sulphuric acid may also be used as an additional reducing agent. Preferably, the boron trifluoride is used as additional reducing agent. In most cases, boron trifluoride can be used as a complex with tetrahydrofuran or the like. The amount used is 1-3 with respect to 1 mol of the alkali metal borohydride.

The reduction is carried out in the presence of a solvent. The solvent may be selected from ether solvents, preferably, tetrahydrofuran. The reaction temperature for the reduction is 0-100° C. and preferably 25-60° C. The reaction time is 1-24 hours.

Step (b) of the process consists of converting the hydroxyl group of compound V into a leaving group. This step can be optional, this means that, compound I can be synthesized with or without conversion of the hydroxyl group into a leaving group.

In an embodiment of the invention, asenapine is synthesized directly by cyclisation of compound V without performing step (b). This cyclisation is achieved by heating a solution of compound V in an organic solvent. The reaction temperature of the cyclisation is between 0° C. and 150° C. Examples of organic solvents are ether solvents, aromatic hydrocarbon solvents, ester solvents, ketone solvents, alcohol solvents, amide solvents, acetonitrile, halogenated solvents and aromatic hydrocarbon solvents.

Sometimes, addition of acid may be required. The acid used may be an organic acid such as para-toluensulfonic acid, methanesulfonic acid, camphorsulfonic acid, benzensulfonic acid or naphtalensulfonic acid. Alternatively, an inorganic acid can be used. Examples of inorganic acids are sulfuric acid, phosphoric acid, hydrochloric acid, etc.

In an embodiment of the invention, step (b) is performed to transform the hydroxyl group of compound V into a leaving group before cyclisation to give asenapine. As indicated before, the leaving group is preferably selected from halogens and activated alcohols, such as sulfonyloxy groups. More preferred are the halogens which include fluorine, chlorine, bromine and iodine. Preferably, the halogen is chlorine or bromine. Introduction of desired halogens is achieved by using specific reagents like thionyl chloride, phosphoryl chloride or carbon tetrachloride or carbon tetrabromide in combination with triphenylphosphine, or triphenylphosphine dibromide or triphenylphosphine diiodide. The amount of leaving group conversion reagent used is 1-5 mol and preferably 1-3 mol with respect to 1 mol of compound V.

The leaving group conversion is usually carried out in the presence of a solvent. The solvent is not particularly restricted. Examples of solvents that can be used are ether solvents, ester solvents, aromatic hydrocarbons and halogenated solvents as those specifically mentioned before.

The reaction temperature for leaving group conversion is between −30° C. and 100° C. and preferably −10° C. to 70° C.

According to an embodiment of the invention, compound V, when treated with a leaving group conversion reagent may undergo cyclisation to yield asenapine. In this case, steps (b) and (c) are performed in a one-pot procedure. That is, compound VI is not isolated and it is subjected to cyclisation in the same reaction vessel.

In these circumstances, the mixture obtained upon completion of the reaction normally contains asenapine as the main product which is subjected to a post-treatment such as filtration, neutralization, washing and extraction. Asenapine may also be isolated by ordinary isolating treatment of the mixture and then it may be purified by ordinary purification means. Then it may also be converted into a salt by conventional procedures known by the skilled person in the art.

Alternatively, compound VI may be isolated and, optionally, purified before being cyclised to give asenapine. This cyclisation may, optionally, be carried out by further allowing compound VI to contact with an organic or inorganic base.

The cyclisation is usually performed in the presence of a solvent. The solvent is not particularly restricted. Examples of solvents that may be used in the cyclisation are ether solvents, amide solvents, ketone solvents, acetonitrile, alcohol solvents, halogenated solvents and aromatic hydrocarbon solvents. These solvents may be used alone or two or more may be used simultaneously. The reaction temperature for cyclisation is between 0° C. to 120° C.

Step (d) of the process consists of the preparation of a salt of asenapine. The mixture obtained upon completion of the cyclisation contains asenapine which may be isolated by ordinary isolating treatment. Asenapine may also be transformed in an acid addition salt. The isolated asenapine or its acid addition salt may be purified by ordinary purification means such as column chromatography or recrystallization, respectively. Moreover, asenapine can be further purified via an acid addition salt thereof that, after being isolated and, optionally, purified is transformed again into asenapine by treatment with an organic or inorganic base.

The acid used to obtain an acid addition salt of asenapine may be for example an organic acid (oxalic acid, fumaric acid, maleic acid, succinic acid, tartaric acid, etc.) or an inorganic acid (hydrochloric acid, hydrobromic acid, sulfuric acid, phosphoric acid or nitric acid).

Another aspect of the invention is directed to an alternative process for the preparation of asenapine or its salts which comprises treating compound of formula I with a reducing agent. This one-pot reaction provides asenapine in acceptable yield, reduced number of chemical steps and without isolating intermediate methylamino compound V. The one-pot reaction is performed in the same reaction vessel.

The reducing agent used in that process may be selected from aluminium hydrides, also referred as "alane" or boron hydrides as described above. The amount of reducing agent used is usually 1-3 with respect to 1 mol of the alkali metal borohydride.

The reduction is carried out in the presence of a solvent. The solvent may be selected from ether solvents, preferably, tetrahydrofuran. The reaction temperature for the reduction is usually 0-100° C. and preferably 25-60° C. The reaction time is 1-24 hours.

The invention also refers to intermediate compounds of the process.

In one aspect, the invention is directed to an amino alcohol compound of formula II:

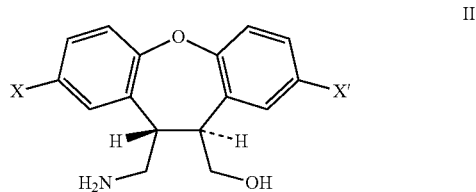

wherein X and X' have the same definitions as above.

In another aspect, the invention is directed to a compound of formula V

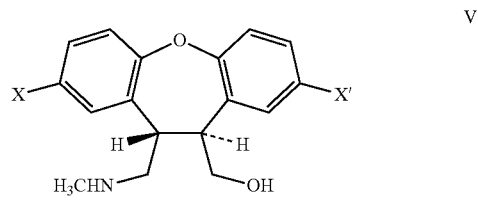

wherein X and X' have the same definitions as above.

Another aspect of the invention is directed to compound of formula VI

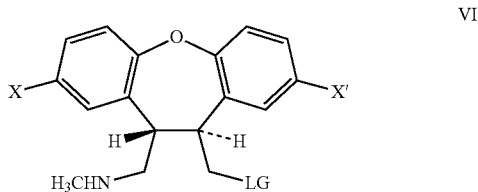

wherein X, X' and LG have the same definitions as above.
Preferred LG are halogen atoms, more preferably, chlorine and bromine. Another aspect of the invention is directed to compound of formula VIII

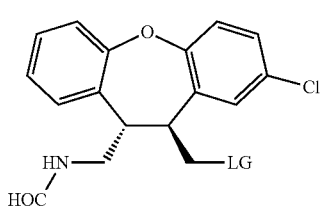

VIII

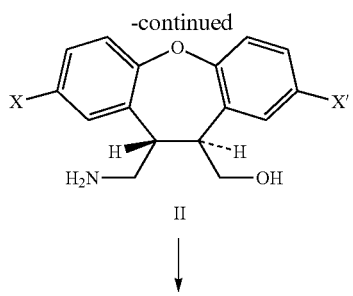

II wherein LG is a leaving group.

In another aspect, the invention provides a process for the preparation of compound of formula I wherein the amino alcohol compound of formula II, is prepared by reduction of both the nitro and ester functions of a compound of formula VII

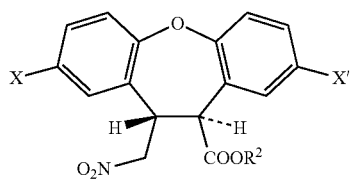

VII wherein X and X' have the same definitions as above and $R^2$ represents a substituted or unsubstituted $C_1$-$C_6$ alkyl, preferably $R^2$ is methyl.

The above process for the preparation of compound I is depicted below in Scheme 4

Scheme 4

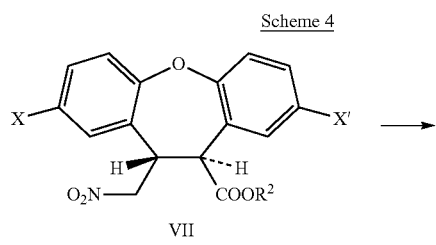

VII

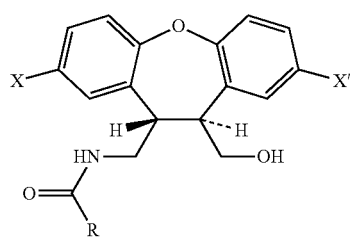

I

The inventors have discovered that the treatment of compound of formula VII with Lithium aluminum hydride (LAH) yields compound of formula II with optimal yields. In most cases, the hydride used is as a complex with tetrahydrofuran, diethyl ether or the like. The amount of reducing agent is 1-10 mol and preferably 1-5 mol with respect to 1 mol of compound II. The mixture obtained upon completion of the reduction of compound VII may be used directly to the next step. However, usually, the mixture is used in the next step after post-treatment such as filtration, neutralization, washing and extraction. Resulting compound II may be isolated and purified by conventional means like crystallization or column chromatography and further converted into compound I.

The process of the invention may be used for the preparation of asenapine and its salts as depicted in the following Scheme 5

Scheme 5

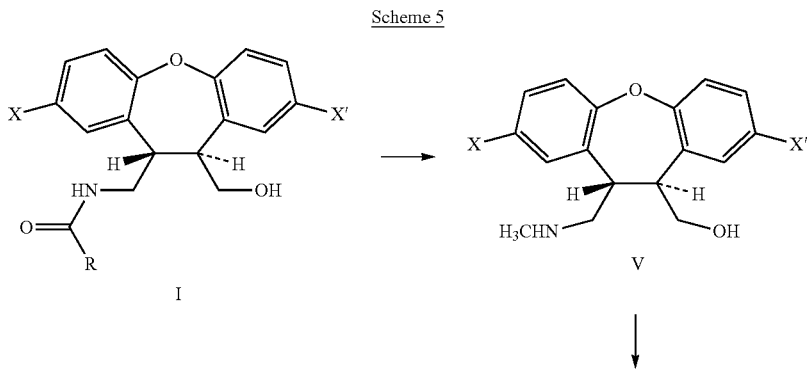

-continued

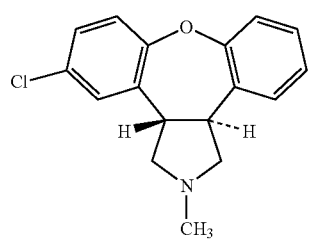 ← 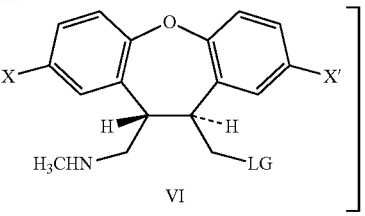

The process of the invention alternatively may be used for the preparation of asenapine and its salts as depicted in the following Scheme 6

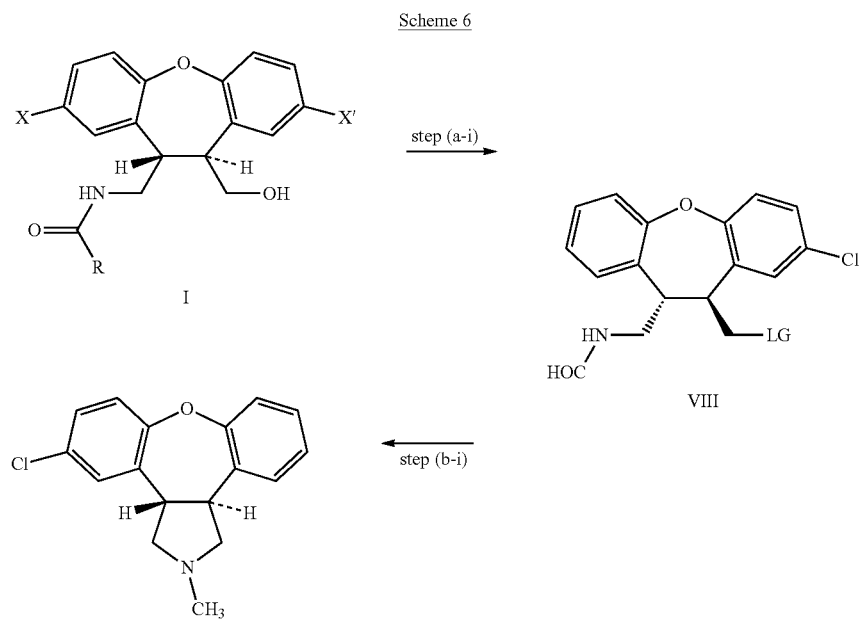

Step (a-i) of the process is performed to convert the hydroxyl group of compound of formula I into a leaving group, before reduction and cyclisation to give asenapine. As previously defined, the leaving group is preferably selected from halogens and activated alcohols, such as sulfonyloxy groups. The most preferred leaving groups are mesylate ($CH_3SO_3^-$), tosylate ($CH_3C_6H_4SO_3^-$), chlorine and bromine. Introduction of desired halogens is achieved by using specific reagents like thionyl chloride, phosphoryl chloride, carbon tetrachloride or carbon tetrabromide in combination with triphenylphophine, triphenylphosphine dibromide or triphenylphosphine diiodide. The preferred reagents are carbon tetrachloride or carbon tetrabromide in combination with triphenylphophine. Introduction of desired sulfonyloxy groups is achieved by using a substituted or unsubstituted alkyl- or aryl-sulfonyl halide, preferably methanesulfonyl chloride ($CH_3SO_3Cl$) or toluenesulfonyl chloride ($CH_3C_6H_4SO_3Cl$). This step is carried out in the presence of a solvent and an organic base. The solvent may be selected from the groups of ethers, amides, ketones, esters, halogenated and aromatic hydrocarbons, as previously defined, preferably, halogenated solvents, most preferably dichloromethane. The organic base may be selected from tertiary amines, aromatic amines, cyclic amidines, alkali metal alkoxides and alkali metal amides, as previously defined. The preferred organic bases are tertiary amines, most preferably triethylamine. The reaction temperature for the derivatization process is between –10° C. and 50° C. and preferably 0° C. to 25° C.

The reduction and cyclisation of the compound of formula VIII to give asenapine, as described in step (b-i), are carried out under the same conditions as previously described for steps (a) and (b).

The reducing agent is selected from boron hydrides or aluminium hydrides, preferably the reducing agent is alkali metal borohydride. The amount of reducing agent used is from 1-10 mol with respect to 1 mol of compound VIII. When alkali metal borohydride is used, as the reducing agent, boron trifluoride tetrahydrofuran complex may also be used, as an additional reducing agent. The amount of additional reducing agent used such as boron trifluoride tetrahydrofuran is 1 to 3 fold the amount of the alkali metal borohydride.

The reaction is carried out in the presence of a solvent. The solvent may be selected from ether solvents, preferably, tetrahydrofuran. The reaction also requires the addition of an inorganic base that may be selected from alkali metal hydroxides, alkali metal carbonates, alkali metal hydrogenocarbonates, ammonia, ammonium carbonate and the like, preferably an alkali metal carbonate. The reaction temperature is between –30° C. and 100° C. and preferably from 0° C. up to 100° C.

Asenapine maleate obtained according to the process of the present invention corresponds to asenapine monoclinic form as described by Funke et al (Arzneim.-Forsch./Drug Res. 40 (1999), 536-539).

The present invention is illustrated in more detail by the following Examples but should not be construed to be limited thereto.

EXAMPLES

Example 1

Preparation of trans-(11-Aminomethyl-2-chloro-10,11-dihydro-dibenzo[b,f]oxepin-10-yl)-methanol (5)

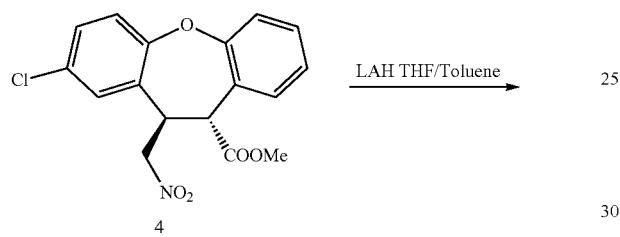

A solution of trans-2-Chloro-11-nitromethyl-10,11-dihydro-dibenzo[b,f]oxepine-10-carboxylic acid methyl ester (4) (4.6 g, 13.23 mmol) in dry THF (23 ml) is added at—15° C. to a mixture of THF (23 ml) and 3.5 M Lithium aluminum hydride (LAH) suspension in THF/Toluene (15.1 ml, 52.9 mmol).

The mixture is stirred at 30° C. for 30 minutes, cooled to −15° C. and sequentially quenched with H$_2$O (2 ml), 15% NaOH (2 ml) and H$_2$O (6 ml).

The solid is filtered, washed with THF (2×23 ml) and the filtrate evaporated to dryness to give 3.60 g (95%) of trans-(11-Aminomethyl-2-chloro-10,11-dihydro-dibenzo[b,f]oxepin-10-yl)-methanol (5) as a pale yellow solid.

$^1$H-RMN (CDCl$_3$, 200 MHz): 1.64 (br s, 3H, exchg. D$_2$O), 2.70-2.80 (m, 1H) 2.87-2.97 (m, 1H), 3.12-3.18 (m, 1H) 3.19-3.36 (m, 1H), 3.44-3.54 (m, 1H), 3.63-3.72 (m, 1H), 7.03-7.26 (m, 7H).

Example 2

Preparation of trans-N-(8-Chloro-11-hydroxymethyl-10,11-dihydro-dibenzo[b,f]oxepin-10-ylmethyl)-formamide (6)

A mixture of Acetic Anhydride (2 ml, 20.7 mmol) and Formic Acid (1.6 ml, 41.4 mmol) is heated to 50° C. for 2 hours. After cooling to 25° C. the mixture is diluted with dichloromethane (15 ml). Next, reaction is cooled to 0° C. and trans-(11-Aminomethyl-2-chloro-10,11-dihydro-dibenzo[b,f]oxepin-10-yl)-methanol (5) (3.00 g, 10.4 mmol) is added and is stirred at 25° C. for one hour.

Reaction is quenched with 10% K$_2$CO$_3$ (20 ml) and organic layer is washed with 10% K$_2$CO$_3$ until pH 9.

Methanol (3 ml) and solid K$_2$CO$_3$ (0.72 g, 5.21 mmol) are added to the organic layer and stirred for 2 hours at room temperature (r.t.). Water (30 ml) is then added and stirred for additional 15 min. Organic layer is then separated, washed with water (2×20 ml) and brine (20 ml) and evaporated to dryness to give 2.45 g (76%) of trans-N-(8-Chloro-11-hydroxymethyl-10,11-dihydro-dibenzo[b,f]oxepin-10-ylmethyl)-formamide (6) as a white solid.

$^1$H-RMN (CDCl$_3$, 200 MHz): 2.23 (br s, 1H, exchg. D$_2$O), 3.30-3.67 (m, 6H), 5.78 (br s, 1H), 7.06-7.23 (m, 7H), 8.10 (s, 1H).

Example 3

Preparation of trans-(2-Chloro-11-methylaminomethyl-10,11-dihydro-dibenzo[b,f]oxepin-10-yl)-methanol (7)

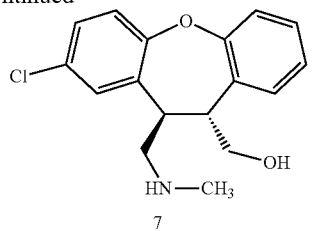

Sodium Borohydride (0.80 g, 21.2 mmol) is added at 0° C. to a solution of trans-N-(8-Chloro-11-hydroxymethyl-10,11-dihydro-dibenzo[b,f]oxepin-10-ylmethyl)-formamide (6) (2.25 g, 7.1 mmol) in dry THF (15 ml). The mixture is stirred for 10'. Next Boron trifluoride tetrahydrofuran complex (4 ml, 34.6 mmol) is added dropwise maintaining temperature below 5° C. Reaction is then stirred at 35° C. for 15 h.

Reaction is then cooled to 0° C. and 3N HCl (15 ml) is added, then is heated to 100° C. and stirred for 30 minutes, during heating about 15 ml of tetrahydrofuran are distilled.

Next is cooled to room temperature and 10% $K_2CO_3$ is added until pH 9, followed by ethyl acetate (30 ml). Organic layer is separated and washed with water, 1M NaOH and brine and evaporated to dryness to obtain 1.85 g (87%) of trans-(2-Chloro-11-methylaminomethyl-10,11-dihydro-dibenzo[b,f]oxepin-10-yl)-methanol (7) as a colorless oil.
$^1$H-RMN (CDCl$_3$, 200 MHz): 1.64 (br s, 2H, exchg. D$_2$O), 2.34 (s, 3H) 2.62-2.78 (m, 1H), 2.80-2.92 (m, 1H) 3.21-3.58 (m, 3H), 3.62-3.74 (m, 1H), 7.03-7.26 (m, 7H).

Example 4

Preparation of Asenapine

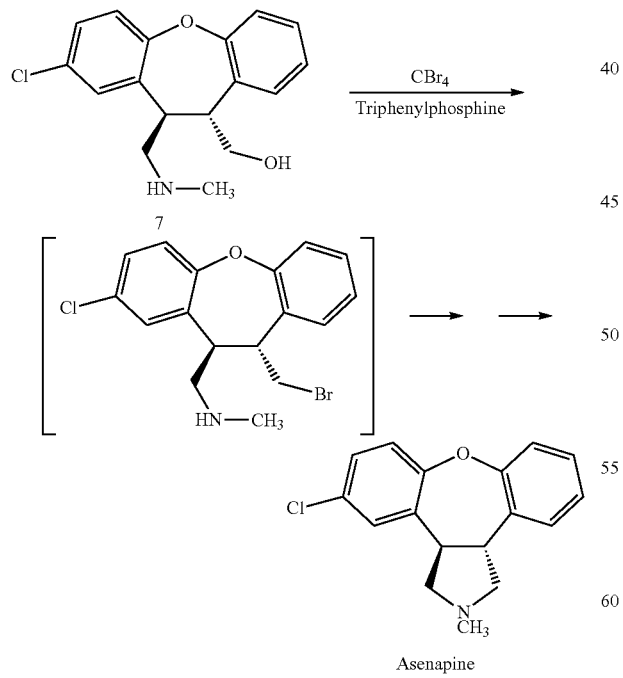

A solution of Carbon Tetrabromide (2.86 g, 8.64 mmol) in Dichloromethane (5 ml) is added at 0° C. to a mixture of trans-(2-Chloro-11-methylaminomethyl-10,11-dihydro-dibenzo[b,f]oxepin-10-yl)-methanol (7) (1.75 g, 5.8 mmol) and Triphenylphosphine (2.26 g, 8.64 mmol) in dichloromethane (10 ml). Reaction is stirred at room temperature overnight.

Reaction is then evaporated and 10 ml of diethylether are added and is stirred for 1 hour at room temperature and 1 hour at 0° C. Triphenylphosphine oxide is then filtered and washed with cold diethylether and organic layers were evaporated to dryness.

Product is purified by flash chromatography (Heptane: Ethyl Acetate 7:3). 1.42 g (86%) of trans-(5-Chloro-2-methyl-2,3,3a,12b-tetrahydro-1H-dibenz[2,3:6,7]oxepino-[4,5-c]pyrrole (Asenapine) are obtained as a slightly yellow oil. 2,1% of cis isomer is observed by HPLC.
$^1$H-RMN (CDCl$_3$, 200 MHz): 2.56 (s, 3H), 3.12-3.18 (m, 4H), 3.61-3.64 (m, 2H), 7.05-7.26 (m, 7H).

Example 5

Preparation of Asenapine Maleate

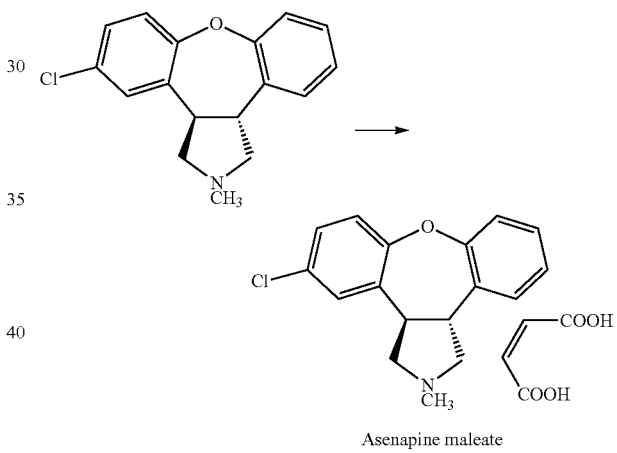

Asenapine maleate trans-(5-Chloro-2-methyl-2,3,3a,12b-tetrahydro-1H-dibenz[2,3:6,7]oxepino-[4,5-c]pyrrole (Asenapine) (1.3 g, 4.5 mmol) is dissolved in absolute ethanol (6.5 ml) at room temperature. Maleic Acid (0.634 g, 5.46 mmol) is then added and stirred until complete dissolution. The solution is seeded with Asenapine Maleate monoclinic form and is stirred overnight at r.t.

Suspension is stirred at 0° C. for one hour, filtered and washed with cold Absolute Ethanol (1 ml). Product is dried for 24 hours at 45° C. 1.63 g of Asenapine Maleate monoclinic form (89%) were obtained as a white solid. No presence of cis isomer is observed by HPLC.
$^1$H-RMN (CD$_3$OH, 200 MHz): 3.14 (s, 3H), 3.79-3.82 (m, 2H), 3.91-3.94 (m, 2H), 4.06-4.11 (m, 2H), 6.23 (s, 2H), 7.16-7.31 (m, 7H).

Example 6

Preparation of Asenapine

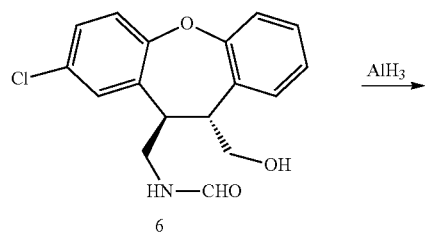

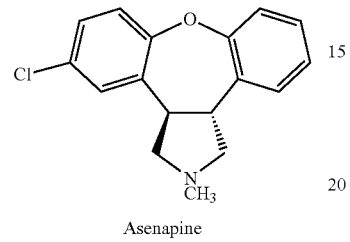

Asenapine

Concentrated sulfuric acid (618 mg, 6.3 mmol) is added carefully at −10° C. to a suspension of lithium aluminum hydride (478 mg, 12.6 mmol) in dry THF (20 mmol). Then a solution of (6) (1.0 g, 3.1 mmol) in THF (5 mL) is added dropwise and the mixture stirred at 40° C. for 6 hr. After quenching sequentially with H$_2$O (0.5 mL), 15% NaOH (0.5 mL) and H$_2$O (1.5 mL), the white precipitate is filtered and the filtrate evaporated. The residue is purified by flash chromatography (Heptane:Ethyl Acetate 7:3) giving 612 mg (69%) of trans-(5-Chloro-2-methyl-2,3,3a,12b-tetrahydro-1H-dibenz[2,3:6,7]oxepino-[4,5-c]pyrrole (Asenapine) as a slightly yellow oil.

$^1$H-RMN (CDCl$_3$, 200 MHz): 2.56 (s, 3H), 3.12-3.18 (m, 4H), 3.61-3.64 (m, 2H), 7.05-7.26 (m, 7H).

Example 7

Preparation of trans-(11-Aminomethyl-8-chloro-10,11-dihydro-dibenzo[b,f]oxepin-10-yl)-methanol (C$_{16}$H$_{16}$ClNO$_2$)

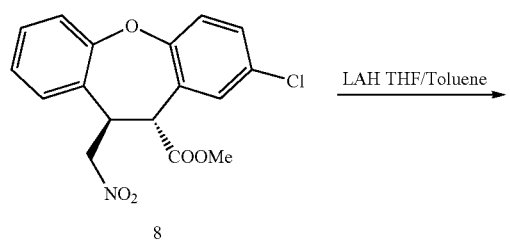

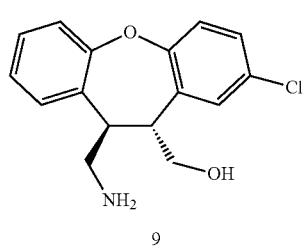

A solution of trans-8-Chloro-11-nitromethyl-10,11-dihydro-dibenzo[b,f]oxepine-10-carboxylic acid methyl ester (8) (5.0 g, 13.23 mmol) in dry THF (25 ml) is added at −15° C. to a mixture of THF (25 ml) and 3.5 M LAH suspension in THF/Toluene (16.4 ml, 57.5 mmol).

The mixture is stirred at 30° C. for 30 minutes, cooled to −15° C. and sequentially quenched with H$_2$O (2 ml), 15% NaOH (2 ml) and H$_2$O (6 ml).

The solid is filtered, washed with THF (2×30 ml) and the filtrate evaporated to dryness to give 3.88 g (93%) of trans-(11-Aminomethyl-2-chloro-10,11-dihydro-dibenzo[b,f]oxepin-10-yl)-methanol (9) as a yellow solid.

Example 8

Preparation of trans-N-(2-Chloro-11-hydroxymethyl-10,11-dihydro-dibenzo[b,f]oxepin-10-ylmethyl)-formamide (C$_{17}$H$_{16}$ClNO$_3$)

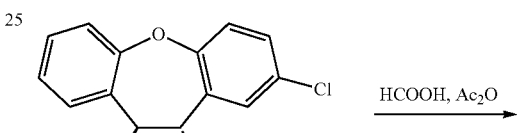

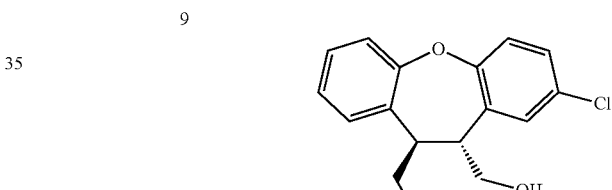

A mixture of Acetic Anhydride (2.3 ml, 24.8 mmol) and Formic Acid (1.9 ml, 49.7 mmol) is heated to 50° C. for 2 hours. After cooling to 25° C. the mixture is diluted with dichloromethane (20 ml). Next, reaction is cooled to 0° C. and trans-(11-Aminomethyl-8-chloro-10,11-dihydro-dibenzo[b,f]oxepin-10-yl)-methanol (9) (3.60 g, 12.4 mmol) is added and is stirred at 25° C. for one hour.

Reaction is quenched with 10% K$_2$CO$_3$ (20 ml) and organic layer is washed with 10% K$_2$CO$_3$ until pH 9.

Methanol (4 ml) and solid K$_2$CO$_3$ (0.86 g, 6.22 mmol) are added to the organic layer and stirred for 2 hours at room temperature. Water (30 ml) is then added and stirred for additional 15 min. Organic layer is then separated, washed with water (2×20 ml) and brine (20 ml) and evaporated to dryness to give 3.20 g (81%) of trans-N-(2-Chloro-11-hydroxymethyl-10,11-dihydro-dibenzo[b,f]oxepin-10-ylmethyl)-formamide (10) as a white solid.

Example 9

Preparation of trans-(8-Chloro-11-methylaminomethyl-10,11-dihydro-dibenzo[b,f]oxepin-10-yl)-methanol ($C_{17}H_{18}ClNO_2$)

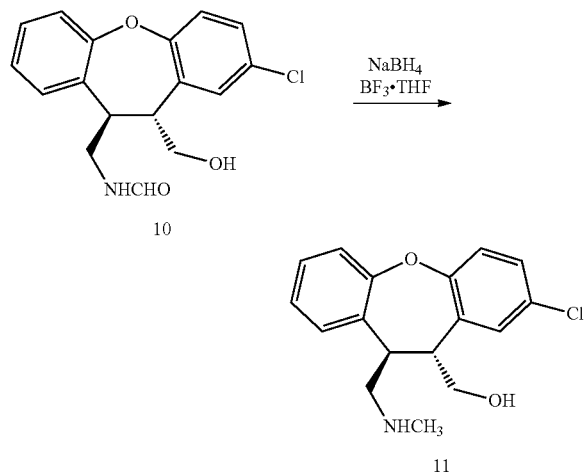

Sodium Borohydride (1.11 g, 29.27 mmol) is added at 0° C. to a solution of trans-(2-Chloro-11-methylaminomethyl-10,11-dihydro-dibenzo[b,f]oxepin-10-yl)-methanol (10) (3.10 g, 9.8 mmol) in dry THF (15 ml). The mixture is stirred for 10 min. Next Boron trifluoride tetrahydrofuran complex (5.4 ml, 48.8 mmol) is added dropwise maintaining temperature below 5° C. Reaction is then stirred at 35° C. for 15 h.

Reaction is then cooled to 0° C. and 3N HCl (10 ml) is added, then is heated to 100° C. and stirred for 30 minutes, during heating about 19 ml of tetrahydrofuran are distilled. Next is cooled to room temperature and 10% $K_2CO_3$ is added until pH 9, followed by ethyl acetate (30 ml). Organic layer is separated and washed with water, 1M NaOH and brine and evaporated to dryness to obtain 2.48 g (84%) of trans-(8-Chloro-11-methylaminomethyl-10,11-dihydro-dibenzo[b,f]oxepin-10-yl)-methanol (11) as a slightly yellow oil.

Example 10

Preparation of Asenapine

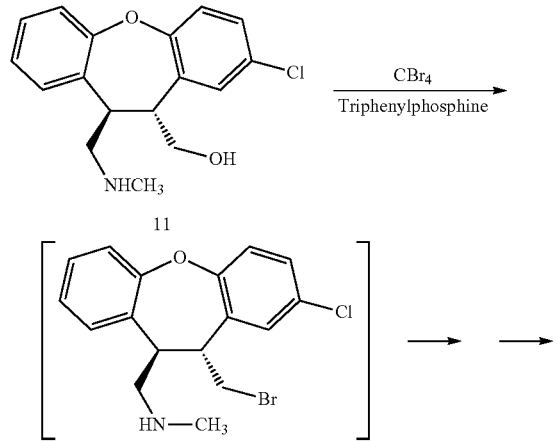

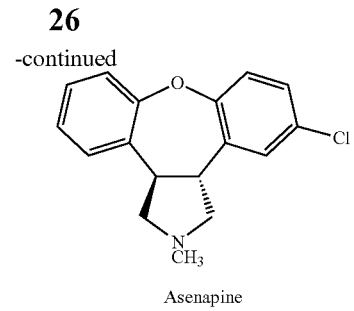

Asenapine

A solution of Carbon Tetrabromide (3.92 g, 11.8 mmol) in Dichloromethane (5 ml) is added at 0° C. to a mixture of trans-(8-Chloro-11-methylaminomethyl-10,11-dihydro-dibenzo[b,f]oxepin-10-yl)-methanol (11) (2.40 g, 7.9 mmol) and Triphenylphosphine (3.10 g, 11.8 mmol) in dichloromethane (10 ml). Reaction is stirred at room temperature overnight.

Reaction is then evaporated and 10 ml of diethylether were added, then is stirred for 1 hour at room temperature and 1 hour at 0° C. Triphenylphosphin oxide is then filtered and washed with cold diethylether and organic layers were evaporated to dryness.

Product is purified by flash chromatography (Heptane: Ethyl Acetate 7:3). 2.06 g (91%) of trans-(5-Chloro-2-methyl-2,3,3a,12b-tetrahydro-1H-dibenz[2,3:6,7]oxepino-[4,5-c]pyrrole (Asenapine) are obtained as a slightly yellow oil. 1.8% of cis isomer is observed by HPLC.

$^1$H-RMN (CDCl$_3$, 200 MHz): 2.56 (s, 3H), 3.12-3.18 (m, 4H), 3.61-3.64 (m, 2H), 7.05-7.26 (m, 7H).

Example 11

Preparation of Methanesulfonic acid trans-2-chloro-11-formylamino methyl-10,11-dihydro-dibenzo[b,f]oxepin-10-ylmethyl Ester

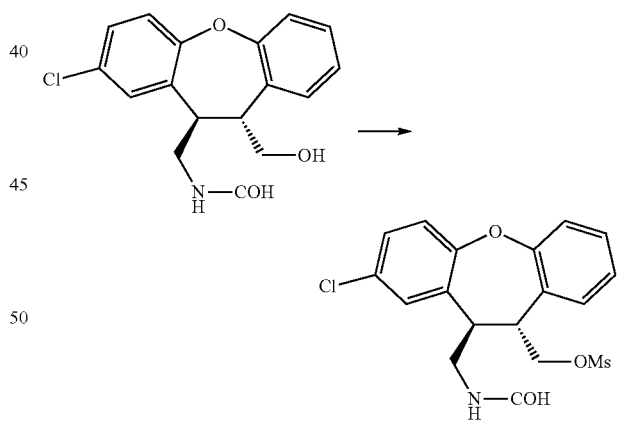

Triethylamine (2.05 g, 20.27 mmol is added to a suspension of trans-N-(8-Chloro-11-hydroxymethyl-10,11-dihydrodibenzo[b,f]oxepin-10-ylmethyl)-formamide (2.30 g, 7.24 mmol) in dichloromethane (23 ml). The suspension is then cooled to 0° C. and methanesulfonyl chloride (1.66 g, 14.48 mmol) is added during 20 minutes, keeping temperature below 5° C. Reaction is then stirred at 5° C. for 30 minutes, until all starting material is dissolved.

Reaction is quenched with 4% NaHCO$_3$ (50 ml) and stirred at 20-25° C. for 30 minutes. After phase separation, the organic layer is washed with water (25 ml) and brine (25 ml) and evaporated to dryness to yield 2.46 g (86%) of methanesulfonic acid trans-2-chloro-11-formylaminomethyl-10,11-dihydro-dibenzo[b,f]oxepin-10-ylmethyl ester as a pale yellow solid that can be used without further purification.

$^1$H-RMN: (CDCl3, 200 MHz): 2.86 (s, 3H), 3.49-3.52 (m, 4H), 4.03 (q, 1H) 4.24 (m, 1H), 6.73 (s, 1H, exchg. D$_2$O), 7.06-7.38 (m, 7H), 8.13 (s, 1H, exchg. D$_2$O).

Example 12

Preparation of Asenapine

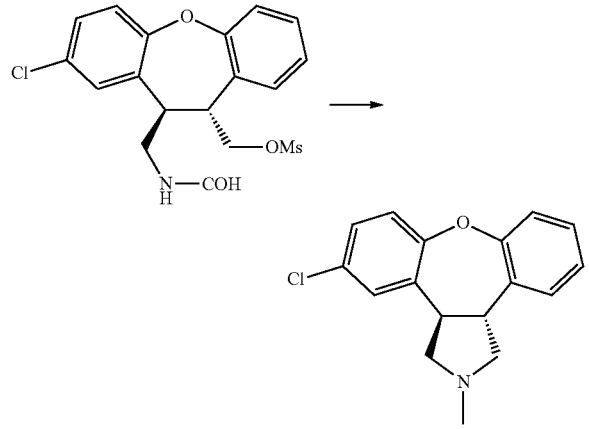

Sodium Borohydride (0.70 g, 18.19 mmol) is added at 0° C. to a solution of methanesulfonic acid trans-2-chloro-11-formylaminomethyl-10,11-dihydro-dibenzo [b,f]oxepin-10-ylmethyl ester (2.40 g, 6.06 mmol) in dry THF (14.4 ml). The mixture is stirred for 10 minutes. Next, boron trifluoride tetrahydrofuran complex (3.3 ml, 30.31 mmol) is added dropwise keeping temperature below 5° C. The reaction is then stirred at 20-25° C. for 15 h.

After cooling to 0° C., 3N HCl (8 ml) is added. The mixture is heated to 100° C. and stirred for 30 minutes, allowing about 15 ml of tetrahydrofuran to distill. Next, it is cooled to 25° C., diluted with Ethyl Acetate (12 ml) and a solution of 10% K$_2$CO$_3$ (25 ml) is added keeping the temperature below 25° C. The reaction is stirred for 1 hour at 20-25° C., filtered and layers separated. The organic layer is washed with 1M NaOH (2×10 ml) and evaporated to dryness to yield 1.65 g (95%) of Asenapine as a clear oil that can be used without further purification. HPLC purity: 92.2%. No presence of cis isomer is observed $^1$H-RMN: (CDCl$_3$, 200 MHz): 2.56 (s, 3H), 3.12-3.18 (m, 4H), 3.61-3.64 (m, 2H), 7.05-7.26 (m, 7H).

Example 13

Preparation of Asenapine Maleate

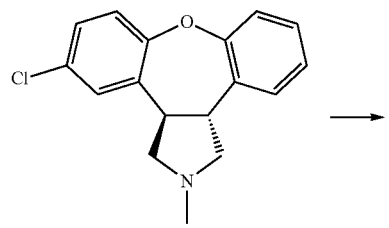

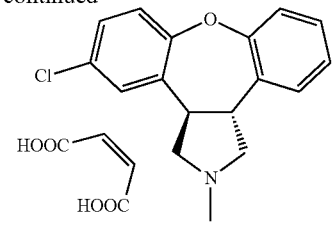

trans-(5-Chloro-2-methyl-2,3,3,12b-tetrahydro-1H-dibenz[2,3;6,7]oxepino-[4,5-c]pyrrole (Asenapine) (1.65 g, 5.77 mmol) is dissolved in absolute ethanol (8.25 ml) and stirred at room temperature for 10 minutes. Maleic Acid (804 mg, 6.93 mmol) is added and stirred until complete dissolution. The solution is seeded with Asenapine Maleate monoclinic form and stirred overnight at room temperature. The obtained suspension is cooled down to 0° C. in an ice bath and stirred for one hour, filtered and washed with cold absolute ethanol (1.65 ml). The obtained product is dried for 24 hours at 45° C.

2.11 g of Asenapine Maleate monoclinic form (91%) is obtained as a white solid. HPLC purity: 99.1%. No presence of cis isomer is observed. $^1$H-RMN: (CDOH, 200 MHz): 3.14 (s, 3H), 3.79-3.82 (m, 2H), 3.91-3.94 (m, 2H), 4.06-4.11 (m, 2H), 6.23 (s, 2H), 7.16-7.31 (m, 7H).

Example 14

Recristalization of Asenapine Maleate 2.11 g (5.25 mmol) of Asenapine Maleate are dissolved in absolute ethanol (8.5 ml) at 65° C. Afterwards, the solution is allowed to cool and seeded with Asenapine Maleate monoclinic form at 40° C. The obtained suspension is cooled to room temperature and stirred for 12 hours, cooled down to 0° C., stirred for 2 hours, filtered and washed with cold absolute ethanol (2.1 ml). The obtained solid is dried for 24 h at 45° C. 1.96 g of Asenapine Maleate monoclinic form (93%) is obtained, as a white solid. HPLC purity: 99.93%. No presence of cis isomer is observed. $^1$H-RMN: (CDOH, 200 MHz): 3.14 (s, 3H), 3.79-3.82 (m, 2H), 3.91-3.94 (m, 2H), 4.06-4.11 (m, 2H), 6.23 (s, 2H), 7.16-7.31 (m, 7H).

What is claimed is:

1. A compound of formula I

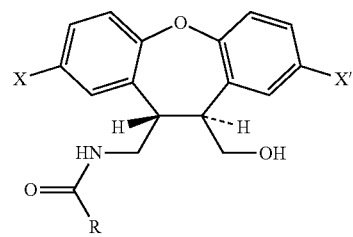

wherein X and X' are different and each independently represents hydrogen or chlorine atom and R is selected from hydrogen or a substituted or unsubstituted C$_1$-C$_6$ alkyloxy group.

2. A compound according to claim 1 selected from the group consisting of trans-N-(8-Chloro-11-hydroxymethyl-10,11-dihydro-dibenzo [b,f]oxepin-10-ylmethyl)-formamide, trans-N-(2-Chloro-11-hydroxymethyl-10,11-dihydro-dibenzo[b,f]oxepin-10-ylmethyl)-formamide, trans-(8-Chloro-11-hydroxymethyl-10,11-dihydro-dibenzo[b,f]

oxepin-10-ylmethyl)-carbamic acid benzyl ester, trans-(2-Chloro-11-hydroxymethyl-10,11-dihydro-dibenzo[b,f]oxepin-10-ylmethyl)-carbamic acid benzyl ester, trans-(8-Chloro-11-hydroxymethyl-10,11-dihydro-dibenzo[b,f]oxepin-10-ylmethyl)-carbamic acid ethyl ester, trans-(2-Chloro-11-hydroxymethyl-10,11-dihydro-dibenzo[b,f]oxepin-10-ylmethyl)-carbamic acid ethyl ester, or a salt thereof.

3. A process for preparing a compound of claim 1 comprising reacting an amino alcohol compound of formula II

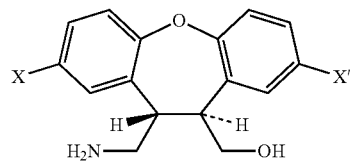

II wherein X and X' are different and each independently represents hydrogen or chlorine atom;
with a formic acid anhydride of formula III or a chloroformate of formula IV

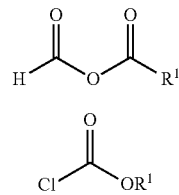

III

IV wherein $R^1$ is a substituted or unsubstituted $C_1$-$C_6$ alkyl.

4. A process according to claim 3 wherein the formic acid anhydride of formula III is selected from the group consisting of formic acetic anhydride, formic propionic anhydride or formic isobutyric anhydride.

5. A process for preparing asenapine, represented by the formula

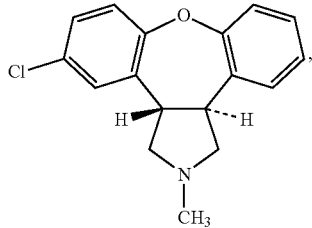

or a salt of asenapine, the process comprising the steps of:
(a) reducing the carbonyl moiety of compound of formula I

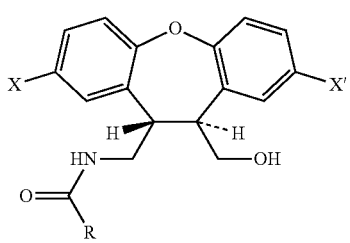

I wherein X and X' are different and each independently represents hydrogen or chlorine atom and R is selected from hydrogen or a substituted or unsubstituted $C_1$-$C_6$ alkyloxy group
to give a methylamino compound of formula V

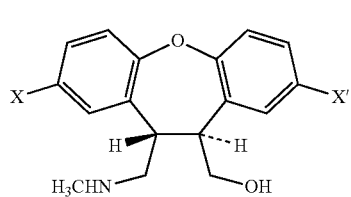

V wherein X and X' are different and each independently represents hydrogen or chlorine atom;
(b) optionally, converting the hydroxyl moiety of compound V into a leaving group to give a compound of formula VI

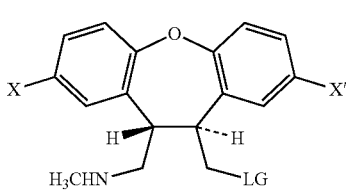

VI wherein X and X' are different and each independently represents hydrogen or chlorine atom and LG is a leaving group;
(c) cyclising the compound of formula V or VI to give asenapine; and
(d) optionally, converting the asenapine to a salt thereof, or
(a-i) converting the hydroxyl moiety of compound of formula I into a leaving group to give a compound of formula VIII

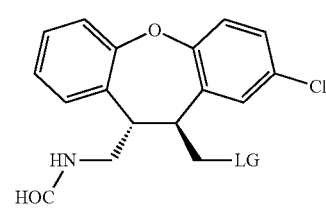

VIII wherein LG is a leaving group
(b-i) reducing and cyclising the compound of formula VIII to give asenapine; and
(c-i) optionally, converting the asenapine to a salt thereof.

6. A process according to claim 5 wherein the reducing agent of step (a) or step (b-i) is a boron hydride or an aluminum hydride.

7. A process according to claim 5 wherein the leaving group is a halogen.

8. A process according to claim 5 wherein steps (b) and (c) are performed in one-pot manner without isolating intermediate compound of formula VI.

9. A process for preparing asenapine or a salt of asenapine comprising treating compound of formula I according to claim 1 with a reducing agent.

10. An amino alcohol compound of formula II:

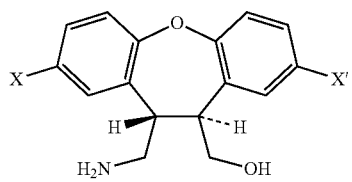

wherein X and X' are different and each independently represents hydrogen or chlorine atom.

11. A compound of formula V

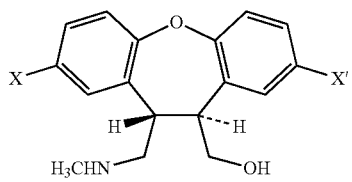

wherein X and X' are different and each independently represents hydrogen or chlorine atom.

12. A compound of formula VI

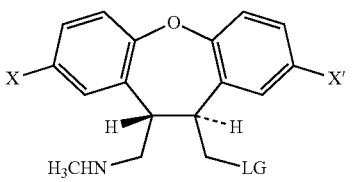

wherein X, X' are different and each independently represents hydrogen or chlorine atom and LG is a leaving group.

13. A compound of formula VIII

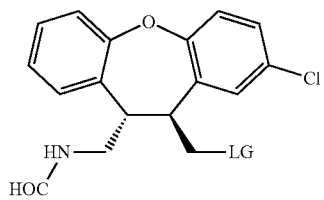

wherein LG is a leaving group.

14. A process according to claim 3 wherein the amino alcohol compound of formula II is prepared by reduction of both the nitro and ester functions of a compound of formula VII

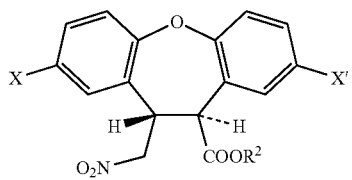

wherein X and X' are different and each independently represents hydrogen or chlorine atom and $R^2$ represents a substituted or unsubstituted $C_1$-$C_6$ alkyl.

* * * * *